United States Patent [19]

Kimura et al.

[11] 4,197,412

[45] Apr. 8, 1980

[54] PROCESS FOR PREPARING TEREPHTHALIC ACID

[75] Inventors: Tsuneo Kimura; Hiroshi Hashizume; Yoshiaki Izumisawa, all of Kitakyushu, Japan

[73] Assignee: Mitsubishi Chemical Industries, Limited, Tokyo, Japan

[21] Appl. No.: 952,193

[22] Filed: Oct. 17, 1978

[30] Foreign Application Priority Data

Nov. 14, 1977 [JP] Japan ................................ 52-136449

[51] Int. Cl.² ............................................. C07C 51/42
[52] U.S. Cl. ................................................... 562/416
[58] Field of Search ......................................... 562/416

[56] References Cited

U.S. PATENT DOCUMENTS 3,970,696  7/1976  Shigeyasu et al. .................... 562/416

*Primary Examiner*—Alan Siegel
*Attorney, Agent, or Firm*—Oblon, Fisher, Spivak, McClelland & Maier

[57] ABSTRACT

A process for the continuous preparation of pure terephthalic acid by oxidation of p-xylene with molecular oxygen in acetic acid solvent comprising conducting the oxidation at a temperature of 205° to 230° C. in the presence of an oxidation catalyst comprising (a) a cobalt compound in an amount of at least 120 ppm and less than 200 ppm as cobalt based on the weight of solvent, (b) a manganese compound sufficient to provide a manganese to cobalt weight ratio of 0.5 to 1.5 and (c) a bromine compound selected from hydrogen bromide, cobalt bromide and manganese bromide in an amount of 200 to 1,000 ppm as bromine based on the weight of solvent, while the water content of the liquid phase of the reaction system is kept at 4 to 14 percent by weight.

10 Claims, No Drawings

PROCESS FOR PREPARING TEREPHTHALIC ACID

BACKGROUND OF THE INVENTION

1. Field of the Invention

This invention relates to a process for producing terephthalic acid by oxidizing p-xylene with molecular oxygen.

2. Description of the Prior Art

Recently, direct polymerization of terephthalic acid and ethylene glycol has been adopted in the preparation of polyethylene terephthalate. It is required that this direct polymerization process use a relatively pure terephthalic acid having the impurity content of not more than 300 ppm as the starting material. Representative of impurities present in terephthalic acid is 4-carboxybenzaldehyde (hereinafter referred to as 4-CBA). Hence, raw terephthalic acid as prepared is usually subjected to purification procedure prior to use in the direct polymerization process.

More recently, there has been proposed a process for preparing terephthalic acid of high purity in one step without additional purification by using a highly active catalyst. This process is attractive from an economic standpoint since it can eliminate the purification step, thus saving greatly the production cost of terephthalic acid. In this process, however, both the amount of solvent combusted and the total amount of catalyst used are greater than those in the prior art process in which a conventional catalyst is used. Therefore, in a commercial sense, there has still been room for improvement in the process just mentioned.

U.S. Pat. No. 4,051,178 issued on Sept. 27, 1977 discloses an improved catalyst for use in the preparation of terephthalic acid, which possesses higher activity and results in lower level of combustion of the solvent.

However, there is a need to provide a further improved process for preparing terephthalic acid of high purity at still lower cost.

SUMMARY OF THE INVENTION

It has now been found that when an Mn/Co weight ratio in the catalyst is in the range of 0.5 to 1.5 and a specific bromine compound is used, high activity of the catalyst and a decrease in the amount of solvent combusted are achieved by maintaining the water content and the temperature of the reaction system within specific ranges, even if the total amount of the catalyst is extremely small.

Thus, in accordance with this invention, there is provided a process for preparing terephthalic acid by oxidation of p-xylene with molecular oxygen in acetic acid solvent, characterized in that the oxidation is conducted at a temperature of 205° to 230° C. in the presence of an oxidation catalyst comprising (a) a cobalt compound in an amount of at least 120 ppm and less than 200 ppm as cobalt based on the weight of solvent, (b) a manganese compound sufficient to provide an Mn/Co weight ratio (as element) of 0.5 to 1.5 and (c) a bromine compound selected from hydrogen bromide, cobalt bromide and manganese bromide in an amount of 200 to 1,000 ppm as bromine based on the weight of solvent, with the water content of the liquid phase of the reaction system being kept at 4% to 14% by weight.

DETAILED DESCRIPTION OF THE PREFERRED EMBODIMENTS

According to the process of this invention, p-xylene is oxidized continuously by passing molecular oxygen through a solution of p-xylene in acetic acid in order to prepare terephthalic acid. For this purpose, any known procedure may be employed, provided that the following conditions are satisfied therewith. The oxidation is carried out at a temperature of 205° to 230° C. and a pressure sufficient to maintain a liquid phase at that temperature, usually, in the range of 10 to 50 kg/cm$^2$. The residence time of the reactant can be relatively short due to the high activity of the catalyst used, and is usually in the range of about 40 to about 150 minutes.

As the molecular oxygen, any gas containing 5 to 100% by volume of molecular oxygen may be used, although usually air is preferred. The amount of oxygen to be supplied is usually 1 to 100 moles and preferably 3 to 100 moles per mole of p-xylene. Particularly, when air is used, the amount of air supplied should be so controlled that the oxygen content of the reactor off-gas is maintained between 1.5 and 8%, preferably between 3 and 5% by volume.

The amount of acetic acid used as the solvent for p-xylene is preferably 2 to 5 times the weight of p-xylene.

It is an essential feature of this invention to use a catalyst comprising specific amounts of cobalt, manganese and bromine compounds. Thus, the catalyst useful in this invention contains a cobalt compound such as cobalt acetate, cobalt naphthate, cobalt bromide or the like. The cobalt compound should be present in an amount of at least 120 ppm, preferably at least 150 ppm and not more than 200 ppm as cobalt based on the weight of solvent.

A manganese compound such as manganese acetate, manganese naphthate or the like should be present in the catalyst in an amount sufficient to provide a manganese/cobalt weight ratio of 0.5 to 1.5, preferably 0.7 to 1.3. The liquid-phase oxidation is conducted at a relatively high temperature in this invention. In such a case, it has been found that, when the amount of manganese is outside the above-defined range, terephthalic acid of high purity cannot be obtained.

The bromine compound used as a catalyst component must be selected from hydrogen bromide, manganese bromide and cobalt bromide, since other bromine compounds such as sodium bromide, potassium bromide, ammonium bromide and tetrabromoethane have low activity and therefore they cannot produce the same results as those of this invention. The bromine compound should be present in an amount of 200 to 1,000 ppm, preferably 400 to 800 ppm as bromine element based on the weight of solvent. Of course, cobalt bromide and manganese bromide can serve as the source of both the bromine component and the heavy metal component.

As is clear from the above, in accordance with the process of this invention, terephthalic acid of high purity can be produced even with the use of smaller amounts of the cobalt, manganese and bromine components as well as with the use of a smaller total amount of the catalyst.

It is another essential feature of the invention to maintain the water content of the liquid phase of the reaction system at 4 to 14%, preferably 6 to 12% by weight. The meritorious effects of this invention cannot be achieved if the water content is outside the above-defined range. More particularly, with a higher water content, either an increase in the activity of the catalyst or a decrease in the amount of the solvent combusted cannot be realized, whereas a lower water content is not practical since in order to maintain that lower water content it is necessary to distill a larger proportion of the solvent for recycle.

The water content of the reaction system can be controlled usually by condensing the condensable reactor off-gas in a condenser and then passing a portion of the condensate to a distillation column to remove water from the solvent prior to recycle of the solvent to the reactor.

The proportion of the condensate to be passed to the distillation column directly affects the water content of the reaction system and therefore it must be so controlled that the water content is kept within the above-defined range. The portion of the condensate not passed to the distillation column is directly recycled into the reactor. In general, if all the condensate is directly recycled into the reactor, the water content of the reaction system is about 17% by weight or above. It has now been found that in order to minimize the amount of the solvent combusted and particularly to develop the high activity of the catalyst, it is necessary to remove enough water to maintain the water content of the reaction system at 14% by weight or below.

Thus, in accordance with this invention, the oxidation of p-xylene with molecular oxygen is conducted under selected conditions including temperature and water content of the reaction system with the use of the decreased total amount of a specific catalyst, whereby the peculiar satisfactory results of this invention, that is, an extremely increased activity of the catalyst with a minimized amount of solvent combusted can be realized.

Having generally described this invention, a more complete understanding can be obtained by reference to certain examples and reference examples which are provided herein for purposes of illustration only and are not intended to be limiting in any manner.

EXAMPLE 1

This example illustrates the case where the water content of the mother liquor of the reaction system is kept at 11.5% by weight.

A 10 l titanium pressure reaction vessel equipped with a reflux condenser, an agitator, a heater, a starting material inlet, a solvent inlet, an air inlet, a reaction slurry outlet and a condensate outlet was charged with a catalyst-containing solvent formulation having the following composition:

| | |
|---|---|
| Acetic acid | 2,990 gr. |
| Cobalt acetate (tetrahydrate) | 2.40 gr. (180 ppm Co) |
| Manganese acetate (tetrahydrate) | 2.53 gr. (180 ppm Mn) |
| Hydrobromic acid (aqueous 47%) | 3.62 gr. (540 ppm Br) |
| Water | 156 gr. (5.0 wt. % $H_2O$) |

Thereafter, at a temperature of 215° C. and a pressure of 25 kg/cm$^2$, p-xylene was fed at a flow rate of 300 g/hr with stirring at 500 rpm and simultaneously air was also fed to the reactor in an amount sufficient to maintain the oxygen content of the reactor off-gas at 4% by volume. Under these conditions, the oxidation reaction was conducted for an hour. Subsequently, a solvent formulation having the same composition as above and glacial acetic acid were fed at flow rates of 900 g/hr and 260 g/hr, respectively, through the solvent inlet, while a condensate was withdrawn at a rate of 260 g/hr through the condensate outlet and sufficient reaction slurry was also withdrawn intermittently every thirty minutes from the reactor to reduce the volume of the reaction slurry to a level of 4.5 l. The oxidation reaction was continued for an additional 18 hours in this way, whereupon the feeding of p-xylene and the solvent was stopped with the oxygen feeding being further continued for 1.5 minutes prior to turn off.

Upon cooling to about 100° C., the reaction slurry was withdrawn from the reactor and then subjected to liquid-solid separation. The terephthalic acid thus isolated was washed by reslurrying it with 3 parts of acetic acid per part of terephthalic acid and stirring the slurry for 20 minutes at 80° C. After the slurry was subjected to liquid-solid separation, the product was finally dried. The 4-CBA content and percent transmission of the terephthalic acid thus obtained were determined. The amount of acetic acid consumed (combusted) during the reaction was also determined. These data are given in Table 1 below.

EXAMPLE 2

This example illustrates the case where the water content of the mother liquor in the reactor is kept at 8.5% by weight.

The reaction was carried out in the same manner as described in Example 1 except that the condensate was withdrawn at a rate of 540 g/hr and that glacial acetic acid was fed at a rate of 540 g/hr.

EXAMPLE 3

This example illustrates the case where the water content of the mother liquor in the reactor is kept at 6.0% by weight.

The reaction was carried out in the same manner as described in Example 1 except that the condensate was withdrawn at a rate of 960 g/hr and that glacial acetic acid was fed at rate of 960 g/hr.

EXAMPLE 4

Following the procedure of Example 1, the reaction was carried out at a temperature of 220° C. and a pressure of 27 kg/cm$^2$ using a catalyst-containing solvent formulation having the following composition:

| | |
|---|---|
| Acetic acid | 2,990 g |
| Cobalt acetate (tetrahydrate) | 2.02 g (150 ppm Co) |
| Manganese acetate (tetrahydrate) | 2.13 g (150 ppm Mn) |
| Hydrobromic acid (aqueous 47%) | 3.05 g (540 ppm Br) |
| Water | 156 g (5.0 wt. % $H_2O$) |

The following controls are given for the purpose of comparison with the foregoing examples.

CONTROL 1

This control illustrates the case where the water content of the mother liquor in the reactor was kept at 18% by weight.

Following the procedure of Example 1, the reaction was first carried out for 2 hours by feeding p-xylene at a flow rate of 120 g/hr together with air to the reactor charged with the same solvent formulation as described in Example 1. Subsequently, a solvent formulation having the same composition as described in Example 1 was fed at a flow rate of 360 g/hr and the reaction was continued for an additional 18 hours with no condensate being withdrawn.

CONTROL 2

This control illustrates the case where the water content of the mother liquor in the reactor is kept at 18% by weight in another way.

The reaction was carried out in the same manner as described in Control 1 except that p-xylene and the solvent formulation were fed at flow rates of 300 g/hr and 900 g/hr, respectively.

CONTROL 3

This control illustrates the case where the water content of the mother liquor in the reactor is kept at 15% by weight.

The reaction was carried out in the same manner as described in Example 1 except that glacial acetic acid was fed at a rate of 75 g/hr and that the condensate was withdrawn at a rate of 75 g/hr.

CONTROL 4

This control illustrates the case where the reaction was conducted at 200° C. with the water content of the mother liquor of the reaction system being kept at 8.5% by weight.

Following the procedure of Example 1, p-xylene was fed at a flow rate of 120 g/hr and oxidized at a temperature of 200° C. and a pressure of 18 kg/cm² for an hour. Subsequently, a solvent formulation having the same composition as in Example 1 and glacial acetic acid were fed at flow rates of 360 g/hr and 210 g/hr, respectively, while the condensate was withdrawn at a rate of 210 g/hr. In other respects, the reaction was carried out in the same way as in Example 1.

Even with the same water content, a lower reaction temperature as in Control 4 compared with Example 1 provides terephthalic acid of inferior quality.

Having now fully described the invention, it will be apparent to one of ordinary skill in the art that many changes and modifications can be made thereto without departing from the sprit or scope of the invention as set forth herein.

What is claimed as new and intended to be covered by Letters Patent is:

1. A process for continuously preparing terephthalic acid by oxidation of p-xylene with molecular oxygen in acetic acid solvent, which comprises conducting the oxidation at a temperature of 205° to 230° C. in the presence of an oxidation catalyst comprising (a) a cobalt compound in an amount of at least 120 ppm and not more than 200 ppm as cobalt based on the weight of solvent, (b) a manganese compound sufficient to provide a manganese/cobalt weight ratio of 0.5 to 1.5 and (c) a bromine compound selected from hydrogen bromide, cobalt bromide and manganese bromide in an amount of 200 to 1,000 ppm as bromine based on the weight of solvent, with the water content of the liquid phase of the reaction system being kept at 4 to 14% by weight.

2. The process of claim 1 wherein the catalyst comprises (a) a cobalt compound in an amount of at least 150 ppm and not more than 200 ppm as cobalt based on the weight of solvent, (b) a manganese compound sufficient to provide a manganese/cobalt weight ratio of 0.7 to 1.3 and (c) a bromine compound selected from hydrogen bromide, cobalt bromide and manganese bromide in an amount of 400 to 800 ppm as bromine based on the weight of solvent.

3. The process of claim 1 wherein the water content

Table 1

| No. | Water content of mother liquor (wt. %) | Maximum residence time (min.) | Quality of TPA* $T_{340}$ (%) | Quality of TPA* 4-CBA (ppm) | Relative amount of acetic acid combusted (Ex. 1 = 1) |
|---|---|---|---|---|---|
| Example 1 | 11.5 | 140 | 92.0 | 180 | 1.0 |
| 2 | 8.5 | 140 | 92.5 | 160 | 1.1 |
| 3 | 6.0 | 140 | 92.0 | 160 | 1.1 |
| 4 | 11.5 | 140 | 92.0 | 160 | 1.0 |
| Control 1 | 18.0 | 300 | 92.0 | 190 | 1.5 |
| 2 | 18.0 | 140 | 87.0 | 420 | 0.7 |
| 3 | 15.0 | 140 | 90.0 | 290 | 0.9 |
| 4 | 8.5 | 300 | 90.0 | 300 | 1.0 |

*TPA = Terephthalic acid

The percent transmission ($T_{340}$) was determined as a solution of 7.5 g of terephthalic acid in 50 cc of aqueous 2 N potassium hydroxide at 340 nm using a spectrophotometer having a cell of 1 cm in light pass length.

The relative amount of acetic acid combusted was determined by measuring the concentrations of CO and $CO_2$ in the reactor off-gas, calculating the amount of acetic acid combusted on the basis of the concentrations of CO and $CO_2$ and comparing the thus obtained value with that of Example 1 which was arbitrarily designated as 1.

It can be seen from the data of Table 1 that in accordance with this invention terephthalic acid of high quality can be obtained with a reduced residence time and a reduced amount of acetic acid combusted. For example, the quality of the terephthalic acid product obtained in Example 1 is comparable to that in Control 1, while the residence time and the amount of acetic acid combusted found in Example 1 are less than those in Control 1.

By comparing Example 1 with Control 2, it can be seen that with the same residence time the procedure of Control 2 cannot provide terephthalic acid of high purity.

of the liquid phase of the reaction system is kept at 6 to 12% by weight.

4. The process of claim 1, wherein said reaction is conducted at a pressure within the range of 10 to 50 kg/cm².

5. The method of claim 1, wherein the amount of molecular oxygen supplied to said reaction is within the range of from 1 to 100 moles per mole of p-xylene.

6. The process of claim 1, wherein the amount of acetic acid employed as said solvent ranges from 2 to 5 times by weight the amount of p-xylene.

7. The process of claim 1, wherein the manganese/cobalt weight ratio ranges from 0.7 to 1.3.

8. The method of claim 1, wherein the amount of bromine compound in said catalyst is such that the amount of bromine ranges from 400 to 800 ppm based on the weight of solvent.

9. The process of claim 1, wherein the water content of said liquid phase ranges from 6 to 12% by weight.

10. The process of claim 1, wherein the amount of cobalt compound in said catalyst is such that the amount of cobalt based on the weight of solvent ranges from 150 ppm to 200 ppm.

* * * * *